(12) United States Patent
Alexander et al.

(10) Patent No.: US 8,338,592 B2
(45) Date of Patent: Dec. 25, 2012

(54) FUSED THIAZOLE DERIVATIVES AS KINASE INHIBITORS

(75) Inventors: Rikki Peter Alexander, Slough (GB); Karen Viviane Lucile Crépy, Slough (GB); Anne Marie Foley, Slough (GB); Richard Jeremy Franklin, Slough (GB)

(73) Assignee: UCB Pharma, S.A., Brussels (BE)

( * ) Notice: Subject to any disclaimer, the term of this patent is extended or adjusted under 35 U.S.C. 154(b) by 48 days.

(21) Appl. No.: 12/666,481

(22) PCT Filed: Jun. 24, 2008

(86) PCT No.: PCT/GB2008/002194
§ 371 (c)(1),
(2), (4) Date: Sep. 22, 2010

(87) PCT Pub. No.: WO2009/001089
PCT Pub. Date: Dec. 31, 2008

(65) Prior Publication Data
US 2011/0003785 A1    Jan. 6, 2011

(30) Foreign Application Priority Data
Jun. 26, 2007 (WO) ................ PCT/GB2007/002390

(51) Int. Cl.
*C07D 413/14* (2006.01)
*A61K 31/535* (2006.01)

(52) U.S. Cl. ..................................... 544/127; 514/234.2

(58) Field of Classification Search ................... 544/127; 514/234.2
See application file for complete search history.

(56) References Cited

FOREIGN PATENT DOCUMENTS
WO    WO 2006/114606 A    11/2006

OTHER PUBLICATIONS

Byrn et al., Solid-State Chemistry of Drugs, 2nd Ed., SSCI, Inc., West Lafayette, IN, Ch. 11, pp. 233-247 (1999).*
Cancer and Metastasis Reviews (1998), 17(1), 91-106.*
Science (1999), vol. 286, 531-537.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/index.html>.*

\* cited by examiner

*Primary Examiner* — Rebecca Anderson
(74) *Attorney, Agent, or Firm* — McDonnell Boehnen Hulbert & Berghoff LLP

(57) ABSTRACT

A series of 6,7-dihydro[1,3]thiazolo[5,4-c]pyridin-4(5H)-one derivatives, which are substituted in the 2-position by a substituted morpholin-4-yl moiety, being selective inhibitors of PI3 kinase enzymes, are accordingly of benefit in medicine, for example in the treatment of inflammatory, autoimmune, cardiovascular, neurodegenerative, metabolic, oncological, nociceptive or ophthalmic conditions.

2 Claims, No Drawings

FUSED THIAZOLE DERIVATIVES AS KINASE INHIBITORS

This application is a US national phase of International Application No. PCT/GB2008/002194 filed on Jun. 24, 2008, which claims the benefit of priority of International Application No. PCT/GB2007/002390 filed on Jun. 26, 2007.

The present invention relates to a class of fused thiazole derivatives, and to their use in therapy. More particularly, the invention provides a family of 6,7-dihydro-[1,3]thiazolo[5,4-c]pyridin-4(5H)-one derivatives, which are substituted in the 2-position by a substituted morpholin-4-yl moiety. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury; head trauma and seizures; metabolic disorders such as obesity and type 2 diabetes; oncological conditions including leukemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2006/114606 describes fused bicyclic thiazole derivatives as selective inhibitors of PI3 kinase enzymes which are accordingly of benefit in medicine, for example in the treatment of inflammatory, autoimmune, cardiovascular, neurodegenerative, metabolic, oncological, nociceptive and ophthalmic conditions.

Various fused thiazole derivatives are disclosed in *Liebigs Annalen der Chemie*, 1986, 780-784; and in *Russian Journal of General Chemistry* (translation of *Zhurnal Obshchei Khimii*), 2000, 70[5], 784-787. However, none of the compounds disclosed in either of those publications corresponds to a compound of the present invention; and no therapeutic utility is ascribed to any of the compounds disclosed therein.

The compounds in accordance with the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The compounds of the invention possess notable advantages in terms of their high potency and selectivity, demonstrable efficacy, and valuable pharmacokinetic properties (including clearance and bioavailability).

The present invention provides a compound of formula (I), or a pharmaceutically acceptable salt or solvate thereof:

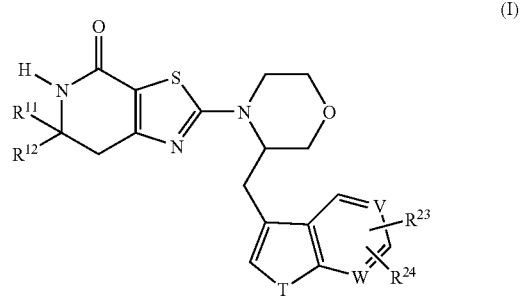

(I)

wherein $R^{11}$ represents hydrogen or $C_{1-6}$ alkyl; and $R^{12}$ represents hydrogen; or $C_{1-6}$ alkyl, $C_{1-6}$ alkoxy, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^{11}$ and $R^{12}$, when taken together with the carbon atom to which they are both attached, represent $C_{3-7}$ cycloalkyl or $C_{3-7}$ heterocycloalkyl, either of which groups may be optionally substituted by one or more substituents;

T represents oxygen or N—$R^{25}$;

V represents carbon or nitrogen;

W represents carbon or nitrogen;

$R^{23}$ represents hydrogen, halogen, cyano, nitro, $C_{1-6}$ alkyl, hydroxy($C_{1-6}$)alkyl, trifluoromethyl, aryl($C_{1-6}$)alkyl, oxazolinyl, triazolyl, hydroxy, $C_{1-6}$ alkoxy, difluoromethoxy, trifluoromethoxy, $C_{3-7}$ cycloalkoxy, $C_{3-7}$ cycloalkyl($C_{1-6}$) alkoxy, morpholinyl($C_{1-6}$)alkoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, azetidinyl, morpholinyl, $C_{2-6}$ alkylcarbonylamino, $C_{2-6}$ alkylcarbonylaminomethyl, $C_{2-6}$ alkoxycarbonylamino, [($C_{2-6}$)alkoxycarbonyl][($C_{1-6}$)alkyl]amino, $C_{1-6}$ alkylsulphonylamino, $C_{2-6}$ alkylcarbonyl, $C_{2-6}$ alkylcarbonyl oxime, $C_{2-6}$ alkylcarbonyl O-(methyl)oxime, trifluoromethylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, [di($C_{1-6}$)alkylamino($C_{1-6}$)alkyl]

aminocarbonyl, di($C_{1-6}$)alkylaminocarbonyl, [($C_{1-6}$)alkyl][cyano($C_{1-6}$)alkyl]aminocarbonyl, [($C_{1-6}$)alkyl][hydroxy($C_{1-6}$)alkyl]aminocarbonyl, [($C_{1-6}$)alkoxy($C_{1-6}$)alkyl][($C_{1-6}$)alkyl]aminocarbonyl, [di($C_{1-6}$)alkylamino($C_{1-6}$)alkyl][($C_{1-6}$)alkyl]aminocarbonyl, $C_{3-7}$ cycloalkyl($C_{1-6}$)alkylaminocarbonyl, aryl($C_{1-6}$)alkylaminocarbonyl, heteroarylaminocarbonyl, heteroaryl($C_{1-6}$)alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, ($C_{1-6}$)alkylpyrrolidinylcarbonyl, $C_{1-6}$ alkoxy($C_{1-6}$)alkylpyrrolidinylcarbonyl, di($C_{1-6}$)alkylaminopyrrolidinylcarbonyl, thiazolidinylcarbonyl, oxothiazolidinylcarbonyl, piperidinylcarbonyl, ($C_{1-6}$) alkylpiperazinylcarbonyl, morpholinylcarbonyl, $C_{1-6}$ alkylsulphonyl, $C_{1-6}$ alkylsulphonylmethyl or di($C_{1-6}$) alkylaminosulphonyl; and $R^{24}$ represents hydrogen, halogen, $C_{1-6}$ alkoxy or di($C_{1-6}$)alkylaminocarbonyl; or $R^{23}$ and $R^{24}$, when situated on adjacent carbon atoms, together represent methylenedioxy or difluoromethylenedioxy; and $R^{25}$ represents $C_{1-6}$ alkyl.

Where any of the groups in the compounds of formula (I) above is stated to be optionally substituted, this group may be unsubstituted, or substituted by one or more substituents. Typically, such groups will be unsubstituted, or substituted by one or two substituents. Suitably, such groups will be unsubstituted or monosubstituted.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, pyrrolyl, indolyl, pyrrolo[2,3-b]pyridinyl, pyrrolo[3,2-c]pyridinyl, pyrazolyl, pyrazolo[1,5-a]pyridinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, pyridazinyl, cinnolinyl, pyrimidinyl, pyrazinyl, quinoxalinyl and chromenyl groups.

The term "halogen" as used herein is intended to include fluorine, chlorine, bromine and iodine atoms, especially fluoro or chloro.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C$=$O$)-enol ($CH$=$CHOH$) tautomers. Formula (I) and the formulae depicted hereinafter are intended to represent all individual tautomers and all possible mixtures thereof, unless stated or shown otherwise.

Typical values of $R^{11}$ include hydrogen, methyl and ethyl. In one embodiment, $R^{11}$ is hydrogen. In another embodiment, $R^{11}$ is $C_{1-6}$ alkyl, especially methyl.

Suitably, $R^{12}$ represents hydrogen; or $C_{1-6}$ alkyl, $C_{3-7}$ cycloalkyl or aryl, any of which groups may be optionally substituted by one or more substituents.

Examples of typical substituents on $R^{12}$ include halogen, cyano, nitro, $C_{1-6}$ alkyl, trifluoromethyl, hydroxy, $C_{1-6}$ alkoxy, difluoromethoxy, trifluoromethoxy, aryloxy, $C_{1-6}$ alkylthio, $C_{1-6}$ alkylsulphonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulphonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl and di($C_{1-6}$)alkylaminosulphonyl; especially halogen, $C_{1-6}$ alkoxy or $C_{1-6}$ alkylthio.

Examples of particular substituents on $R^{12}$ include fluoro, chloro, bromo, cyano, nitro, methyl, trifluoromethyl, hydroxy, methoxy, difluoromethoxy, trifluoromethoxy, phenoxy, methylthio, methylsulphonyl, amino, methylamino, dimethylamino, acetylamino, methoxycarbonylamino, methylsulphonylamino, formyl, acetyl, carboxy, methoxycarbonyl, aminocarbonyl, methylaminocarbonyl, dimethylaminocarbonyl, aminosulphonyl, methylaminosulphonyl and dimethylaminosulphonyl; especially chloro, methoxy or methylthio.

Typical values of $R^{12}$ include hydrogen, methyl, n-propyl, isopropyl, isobutyl, cyclohexyl and phenyl. A particular value of $R^{12}$ is methyl.

Alternatively, $R^{11}$ and $R^{12}$ may together form an optionally substituted spiro linkage. Thus, $R^{11}$ and $R^{12}$, when taken together with the carbon atom to which they are both attached, may represent $C_{3-7}$ cycloalkyl or $C_{3-7}$ heterocycloalkyl, either of which groups may be unsubstituted, or substituted by one or more, typically by one or two, substituents. In this context, $R^{11}$ and $R^{12}$, when taken together with the carbon atom to which they are both attached, may suitably represent an optionally substituted cyclopentyl, cyclohexyl, pyrrolidine or piperidine ring.

In a preferred embodiment, T is N—$R^{25}$. In another embodiment, T is oxygen.

In a preferred embodiment, V is carbon. In another embodiment, V is nitrogen.

In a preferred embodiment, W is carbon. In another embodiment, W is nitrogen.

The present invention also provides a compound of formula (I) as depicted above, or a pharmaceutically acceptable salt or solvate thereof, wherein $R^{23}$ represents hydrogen, halogen, cyano, nitro, $C_{1-6}$ alkyl, hydroxy($C_{1-6}$)alkyl, trifluoromethyl, aryl($C_{1-6}$)alkyl, hydroxy, $C_{1-6}$ alkoxy, difluoromethoxy, trifluoromethoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl][hydroxy($C_{1-6}$)alkyl]aminocarbonyl, aryl($C_{1-6}$)alkylaminocarbonyl, azetidinylcarbonyl, pyrrolidinylcarbonyl, piperidinylcarbonyl, ($C_{1-6}$)alkylpiperazinylcarbonyl or morpholinylcarbonyl.

The present invention further provides a compound of formula (I) as depicted above, or a pharmaceutically acceptable salt or solvate thereof, wherein $R^{23}$ represents hydrogen, halogen, cyano, $C_{1-6}$ alkyl, hydroxy($C_{1-6}$)alkyl, trifluoromethyl, aryl($C_{1-6}$)alkyl, hydroxy, $C_{1-6}$ alkoxy, trifluoromethoxy, aryloxy, aryl($C_{1-6}$)alkoxy, $C_{1-6}$ alkylthio, $C_{1-6}$ alkylsulphinyl, arylsulphinyl, arylsulphonyl, $C_{1-6}$ alkylsulphonyloxy, amino, $C_{2-6}$ alkylcarbonylamino, $C_{1-6}$ alkylsulphonylamino, $C_{2-6}$ alkylcarbonyl or aminocarbonyl.

Particular values of $R^{23}$ include hydrogen, halogen, cyano, nitro, oxazolinyl, triazolyl, $C_{1-6}$ alkoxy, difluoromethoxy, trifluoromethoxy, $C_{3-7}$ cycloalkoxy, $C_{3-7}$ cycloalkyl($C_{1-6}$)alkoxy, morpholinyl($C_{1-6}$)alkoxy, azetidinyl, morpholinyl, $C_{2-6}$ alkylcarbonylamino, $C_{2-6}$ alkylcarbonylaminomethyl, $C_{2-6}$ alkoxycarbonylamino, [($C_{2-6}$)alkoxycarbonyl][($C_{1-6}$)alkyl]amino, $C_{1-6}$ alkylsulphonylamino, $C_{2-6}$ alkylcarbonyl, $C_{2-6}$ alkylcarbonyl oxime, $C_{2-6}$ alkylcarbonyl O-(methyl)oxime, trifluoromethylcarbonyl, carboxy, $C_{2-6}$ alkoxycarbonyl, aminocarbonyl, $C_{1-6}$ alkylaminocarbonyl, [hydroxy($C_{1-6}$)alkyl]aminocarbonyl, [di($C_{1-6}$)alkylamino($C_{1-6}$)alkyl]aminocarbonyl, di($C_{1-6}$)alkylaminocarbonyl, [($C_{1-6}$)alkyl][cyano($C_{1-6}$)alkyl]aminocarbonyl, [($C_{1-6}$)alkyl][hydroxy($C_{1-6}$)alkyl]aminocarbonyl, [($C_{1-6}$)alkoxy($C_{1-6}$)alkyl][($C_{1-6}$)alkyl]aminocarbonyl, [di($C_{1-6}$)alkylamino($C_{1-6}$)alkyl][($C_{1-6}$)alkyl]aminocarbonyl, $C_{3-7}$ cycloalkyl($C_{1-6}$)alkylaminocarbonyl, aryl($C_{1-6}$)alkylaminocarbonyl, heteroarylaminocarbonyl, heteroaryl($C_{1-6}$)alkylaminocarbonyl, azetidinylcarbonyl, hydroxyazetidinylcarbonyl, aminoazetidinylcarbonyl, $C_{2-6}$ alkoxycarbonylaminoazetidinylcarbonyl, pyrrolidinylcarbonyl, ($C_{1-6}$)alkylpyrrolidinylcarbonyl, $C_{1-6}$ alkoxy($C_{1-6}$)alkylpyrrolidinylcarbonyl, di($C_{1-6}$)alkylaminopyrrolidinylcarbonyl, thiazolidinylcarbonyl, oxothiazolidinylcarbonyl, piperidinylcarbonyl, ($C_{1-6}$)alkylpiperazinylcarbonyl, morpholinylcarbonyl, $C_{1-6}$ alkylsulphonyl, $C_{1-6}$ alkylsulphonylmethyl and di($C_{1-6}$)alkylaminosulphonyl.

Typical values of $R^{23}$ include hydrogen, halogen, nitro, difluoromethoxy, trifluoromethoxy, carboxy, $C_{2-6}$ alkoxycarbonyl, $C_{1-6}$ alkylaminocarbonyl, [hydroxy($C_{1-6}$)alkyl]aminocarbonyl, di($C_{1-6}$)alkylaminocarbonyl, [($C_{1-6}$)alkyl][hydroxy($C_{1-6}$)alkyl]aminocarbonyl, aryl($C_{1-6}$)alkylaminocarbonyl, azetidinylcarbonyl, piperidinylcarbonyl, ($C_{1-6}$)alkylpiperazinylcarbonyl and morpholinylcarbonyl.

Suitable values of $R^{23}$ include hydrogen, $C_{1-6}$ alkyl, hydroxy, aryl($C_{1-6}$)alkoxy and $C_{1-6}$ alkylsulphonyloxy.

Illustrative values of $R^{23}$ include hydrogen, fluoro, chloro, bromo, cyano, nitro, methyl, hydroxymethyl, trifluoromethyl, benzyl, hydroxy, methoxy, ethoxy, difluoromethoxy, trifluoromethoxy, phenoxy, benzyloxy, methylthio, methylsulphinyl, phenylsulphinyl, phenylsulphonyl, methylsulphonyloxy, amino, acetylamino, methylsulphonylamino, acetyl, carboxy, methoxycarbonyl, aminocarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, pyrrolidinylcarbonyl, piperidinylcarbonyl, methylpiperazinylcarbonyl and morpholinylcarbonyl.

Specific values of $R^{23}$ include hydrogen, fluoro, chloro, bromo, cyano, methyl, hydroxymethyl, trifluoromethyl, benzyl, hydroxy, methoxy, ethoxy, trifluoromethoxy, phenoxy, benzyloxy, methylthio, methylsulphinyl, phenylsulphinyl, phenylsulphonyl, methylsulphonyloxy, amino, acetylamino, methylsulphonylamino, acetyl and aminocarbonyl; especially hydrogen, methyl, hydroxy, benzyloxy or methylsulphonyloxy.

Definitive values of $R^{23}$ include hydrogen, fluoro, chloro, cyano, nitro, oxazolinyl, triazolyl, methoxy, difluoromethoxy, trifluoromethoxy, cyclobutyloxy, cyclopropylmethoxy, morpholinylethoxy, azetidinyl, morpholinyl, acetylamino, acetylaminomethyl, methoxycarbonylamino, N-methoxycarbonyl-N-methylamino, methylsulphonylamino, acetyl, acetyl oxime, acetyl O-(methyl)oxime, trifluoromethylcarbonyl, carboxy, methoxycarbonyl, aminocarbonyl, methylaminocarbonyl, (hydroxyethyl)aminocarbonyl, (dimethylaminoethyl)aminocarbonyl, (1-hydroxyprop-2-yl)aminocarbonyl, dimethylaminocarbonyl, N-(cyanomethyl)-N-methylaminocarbonyl, N-(cyanoethyl)-N-methylaminocarbonyl, N-(hydroxyethyl)-N-methylaminocarbonyl, N-(methoxyethyl)-N-methylaminocarbonyl, N-(dimethylaminoethyl)-N-methylaminocarbonyl, N-isopropyl-N-methylaminocarbonyl, diethylaminocarbonyl, cyclopropylmethylaminocarbonyl, benzylaminocarbonyl, pyrazolylaminocarbonyl, pyridinylmethylaminocarbonyl, azetidinylcarbonyl, hydroxyazetidinylcarbonyl, aminoazetidinylcarbonyl, tert-butoxycarbonylaminoazetidinylcarbonyl, pyrrolidinylcarbonyl, methylpyrrolidinylcarbonyl, methoxymethylpyrrolidinylcarbonyl, dimethylaminopyrrolidinylcarbonyl, thiazolidinylcarbonyl, oxothiazolidinylcarbonyl, piperidinylcarbonyl, methylpiperazinylcarbonyl, morpholinylcarbonyl, methylsulphonyl, methylsulphonylmethyl and dimethylaminosulphonyl.

Selected values of $R^{23}$ include hydrogen, fluoro, nitro, difluoromethoxy, trifluoromethoxy, carboxy, methoxycarbonyl, methylaminocarbonyl, (hydroxyethyl)aminocarbonyl, dimethylaminocarbonyl, N-(hydroxyethyl)-N-methylaminocarbonyl, benzylaminocarbonyl, azetidinylcarbonyl, piperidinylcarbonyl, methylpiperazinylcarbonyl and morpholinylcarbonyl.

Typically, $R^{23}$ may represent hydrogen, cyano, carboxy, $C_{2-6}$ alkoxycarbonyl, di($C_{1-6}$)alkylaminocarbonyl, [($C_{1-6}$)alkyl][cyano($C_{1-6}$)alkyl]aminocarbonyl, [($C_{1-6}$)alkoxy($C_{1-6}$)alkyl][($C_{1-6}$)alkyl]aminocarbonyl or azetidinylcarbonyl.

Suitably, $R^{23}$ may represent hydrogen, cyano, carboxy, methoxycarbonyl, dimethylaminocarbonyl, N-(cyanomethyl)-N-methylaminocarbonyl, N-(methoxyethyl)-N-methylaminocarbonyl or azetidinylcarbonyl.

A particular value of $R^{23}$ is hydrogen. Another value of $R^{23}$ is cyano. Another value of $R^{23}$ is carboxy. Another value of $R^{23}$ is $C_{2-6}$ alkoxycarbonyl, especially methoxycarbonyl. A further value of $R^{23}$ is di($C_{1-6}$)alkylaminocarbonyl, especially dimethylaminocarbonyl. A further value of $R^{23}$ is [($C_{1-6}$)alkyl][cyano($C_{1-6}$)alkyl]aminocarbonyl, especially N-(cyanomethyl)-N-methylaminocarbonyl. A still further value of $R^{23}$ is [($C_{1-6}$)alkoxy($C_{1-6}$)alkyl][($C_{1-6}$)alkyl]aminocarbonyl, especially N-(methoxyethyl)-N-methylaminocarbonyl. An additional value of $R^{23}$ is azetidinylcarbonyl.

Definitive values of $R^{24}$ include hydrogen, chloro, methoxy and dimethylaminocarbonyl. A particular value of $R^{24}$ is hydrogen.

In one embodiment, $R^{25}$ is suitably methyl.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as microionized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (II) with a compound of formula (III):

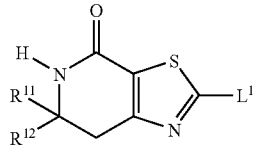

(II)

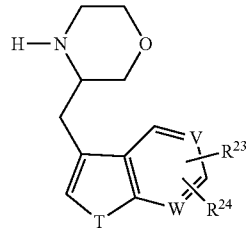

(III)

wherein $R^{11}$, $R^{12}$, T, V, W, $R^{23}$ and $R^{24}$ are as defined above, and $L^1$ represents a suitable leaving group.

The leaving group $L^1$ is typically a halogen atom, e.g. bromo.

The reaction is conveniently effected at an elevated temperature in a suitable solvent, e.g. a lower alkanol such as isopropanol or a cyclic ether such as tetrahydrofuran, typically under basic conditions, e.g. in the presence of an organic base such as N,N-diisopropylethylamine or 2,6-lutidine.

Alternatively, the reaction may be effected at an elevated temperature in a solvent such as 2-ethoxyethanol in the presence of a catalytic quantity of a mineral acid, e.g. concentrated hydrochloric acid.

In another alternative, the reaction may be effected at an elevated temperature in a suitable solvent, e.g. a cyclic ether such as tetrahydrofuran, or an aromatic solvent such as toluene, typically under basic conditions, e.g. in the presence of an inorganic base such as sodium tert-butoxide, in the presence of a transition metal catalyst. The transition metal catalyst is suitably palladium(II) acetate, in which case the reaction will ideally be performed in the presence of tert-butylphosphonium tetrafluoroborate or dicyclohexyl diphenylphosphine.

The intermediates of formula (II) above wherein $L^1$ is bromo may be prepared from a compound of formula (IV):

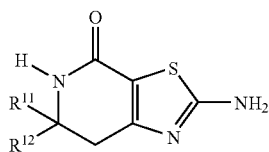

(IV)

wherein $R^{11}$ and $R^{12}$ are as defined above; by diazotization/bromination.

The reaction is conveniently effected by stirring compound (IV) with tert-butyl nitrite and copper(II) bromide in a suitable solvent, e.g. acetonitrile.

The intermediates of formula (IV) above may be prepared by reacting thiourea with a compound of formula (V):

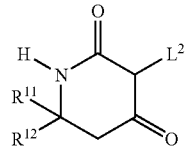

(V)

wherein $R^{11}$ and $R^{12}$ are as defined above, and $L^2$ represents a suitable leaving group.

The leaving group $L^2$ is typically a halogen atom, e.g. bromo.

The reaction is conveniently effected at an elevated temperature in a suitable solvent, e.g. a cyclic ether such as tetrahydrofuran, typically under basic conditions, e.g. in the presence of an organic base such as N,N-diisopropylethylamine.

Alternatively, the reaction may be accomplished by heating the reactants in a lower alkanol solvent, e.g. a $C_{1-6}$ alkyl alcohol such as ethanol.

In another procedure, the compounds of formula (I) may be prepared by a process which comprises reacting a compound of formula (V) as defined above with a compound of formula (VI):

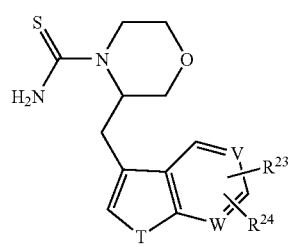

(VI)

wherein T, V, W, $R^{23}$ and $R^{24}$ are as defined above; under conditions analogous to those described above for the reaction between thiourea and compound (V).

In an additional procedure, the compounds of formula (I) wherein T is oxygen may be prepared by a process which comprises reacting a compound of formula (VII) with a compound of formula (VIII):

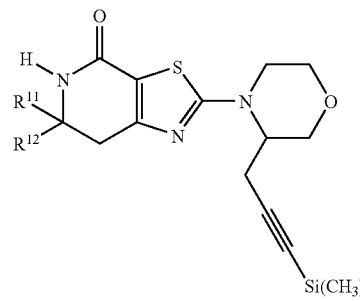

(VII)

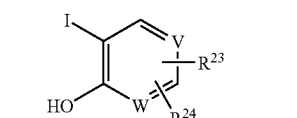

(VIII)

wherein $R^{11}$, $R^{12}$, V, W, $R^{23}$ and $R^{24}$ are as defined above; in the presence of a transition metal catalyst; followed by removal of the trimethylsilyl moiety from the 2-position of the resulting cycloaddition product.

The transition metal catalyst of use in the reaction between compounds (VII) and (VIII) is suitably palladium(II) acetate, in which case the reaction may conveniently be effected at an elevated temperature in a suitable solvent, e.g. a dipolar aprotic solvent such as N,N-dimethylformamide, in the presence of lithium chloride and a base, typically an inorganic base, e.g. an alkaline earth metal carbonate such as sodium carbonate.

Removal of the trimethylsilyl moiety from the resulting cycloaddition product may be effected by treatment with an acid, e.g. a mineral acid such as hydrochloric acid.

Alternatively, the trimethylsilyl moiety may be removed by treatment with a base, typically an inorganic base, e.g. an alkali metal hydroxide such as lithium hydroxide.

The intermediates of formula (VII) above may be prepared by reacting a compound of formula (V) as defined above with the compound of formula (IX):

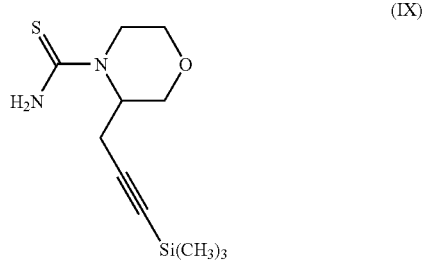

under conditions analogous to those described above for the reaction between compounds (V) and (VI).

Where they are not commercially available, the starting materials of formula (III), (V), (VI), (VIII) and (IX) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein $R^{23}$ represents $C_{2-6}$ alkoxycarbonyl, e.g. methoxycarbonyl, may be converted into the corresponding compound wherein $R^{23}$ represents carboxy (—$CO_2H$) under standard saponification conditions, e.g. by treatment with a base such as lithium hydroxide. A compound of formula (I) wherein $R^{23}$ represents carboxy (—$CO_2H$) may be converted into the corresponding compound wherein $R^{23}$ contains an amido group, e.g. methylaminocarbonyl, 2-hydroxyethylaminocarbonyl, dimethylaminocarbonyl, N-(cyanomethyl)-N-methylaminocarbonyl, N-(2-hydroxyethyl)-N-methylaminocarbonyl, N-(2-methoxyethyl)-N-methylaminocarbonyl, benzylaminocarbonyl, azetidin-1-ylcarbonyl, pyrrolidin-1-ylcarbonyl, piperidin-1-ylcarbonyl, 4-methylpiperazin-1-ylcarbonyl or morpholin-4-ylcarbonyl, by a two-stage procedure which comprises (i) treatment of the carboxy derivative with pentafluorophenol in the presence of a condensing agent such as 1-(3-dimethylaminopropyl)-3-ethylcarbodiimide; and (ii) reaction of the pentafluorophenyl ester thereby obtained with the appropriate amine, e.g. methylamine, 2-hydroxyethylamine, dimethylamine, N-(cyanomethyl)-N-methylamine, N-(2-hydroxyethyl)-N-methylamine, N-(2-methoxyethyl)-N-methylamine, benzylamine, azetidine, pyrrolidine, piperidine, 1-methylpiperazine or morpholine.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$.

When tested in the above assay, the compounds of the accompanying Examples were all found to possess $IC_{50}$ values for inhibition of activity of human PI3Kα and/or PI3Kβ and/or PI3Kγ and/or PI3Kδ of 50 μM or better.

EXAMPLES

Abbreviations
DCM: dichloromethane DMF: N,N-dimethylformamide
DMSO: dimethylsulphoxide Et: ethyl
Et$_2$O: diethyl ether THF: tetrahydrofuran
r.t.: room temperature sat.: saturated
MeCN: acetonitrile EtOAc: ethyl acetate
MeOH: methanol AcOH: acetic acid
EtOH: ethanol IPA: isopropyl alcohol
RT: retention time Me: methyl
h: hour conc.: concentrated
SiO$_2$: silica br.: broad
w or wt: weight M: mass
$^t$Bu: tert-butyl v: volume
NBS: N-bromosuccinimide
brine: saturated aqueous sodium chloride solution
HPLC: High Performance Liquid Chromatography
LCMS: Liquid Chromatography Mass Spectrometry
DIPEA: N,N-diisopropylethylamine
ES+: Electrospray Positive Ionisation
ES−: Electrospray Negative Ionisation
EDC: 1-(3-dimethylaminopropyl)-3-ethylcarbodiimide hydrochloride
DMPU: 1,3-dimethyl-3,4,5,6-tetrahydro-2(1H)-pyrimidinone Analytical Conditions All NMRs were obtained either at 300 MHz or 400 MHz.

Compounds were named with the aid of ACD Labs Name (v. 7.0, 9.0 or 10.0) supplied by Advanced Chemical Development, Toronto, Canada.

All reactions involving air- or moisture-sensitive reagents were performed under a nitrogen atmosphere using dried solvents and glassware.

Compound purities and retention times were determined by LCMS using one of the Methods 1-9 below.

Preparative HPLC for compounds that required it was performed using one of the Methods 10-13 below.

Method 1: Luna C18(2) 100×4.6 mm, 5 μm column. Mobile phase A: 99.92% water, 0.08% formic acid. Mobile phase B: 99.92% MeCN, 0.08% formic acid.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 2: Luna C18(2) 100×4.6 mm, 5 μm column. Mobile phase A: 5 mM NH$_4$OAc, pH 5.8. Mobile phase B: 95:5 MeCN: 100 mM NH$_4$OAc, pH 5.8.

Gradient program (flow rate 3.0 mL/min, column temperature 35° C.):

| Time | A % | B % |
|---|---|---|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Method 3: Gemini C18 50×4.6 mm, 5 μm column. Mobile phase A: 99.9% 10 mM ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
|---|---|---|
| 0.00 | 95.0 | 5.0 |
| 2.00 | 5.0 | 95.0 |
| 5.50 | 5.0 | 95.0 |

Method 4: Gemini C18 50×4.6 mm, 5 μm column. Mobile phase A: 99.9% 10 mM ammonium formate, 0.1% ammonia. Mobile phase B: 94.9% MeCN, 0.1% ammonia, 5% mobile phase A.

Gradient program (flow rate 3.0 mL/min, column temperature 40° C.):

| Time | A % | B % |
|---|---|---|
| 0.00 | 95.0 | 5.0 |
| 2.00 | 5.0 | 95.0 |
| 5.50 | 5.0 | 95.0 |

Method 5: Gemini C18 50×4.6 mm, 5 μm column. Mobile phase A: 99.9% ammonium formate, 0.1% formic acid. Mobile phase B: 94.9% MeCN, 0.1% formic acid, 5% mobile phase A.

Gradient program (flow rate 0.9 mL/min, column temperature 40° C.):

| Time | A % | B % |
|---|---|---|
| 0.00 | 95.0 | 5.0 |
| 2.00 | 5.0 | 95.0 |
| 4.00 | 5.0 | 95.0 |

Method 6: Gemini C18 30×3.0 mm, 3 μm column. Mobile phase A: 99.9% 10 mM ammonium formate, 0.1% formic acid. Mobile phase B: 94.9% MeCN, 0.1% formic acid, 5% mobile phase A.

Gradient program (flow rate 1.2 mL/min, column temperature 40° C.):

| Time | A % | B % |
|---|---|---|
| 0.00 | 95.0 | 5.0 |
| 4.00 | 5.0 | 95.0 |
| 5.50 | 5.0 | 95.0 |

Method 7: Gemini C18 30×3.0 mm, 3 μm column. Mobile phase A: 99.9% 10 mM ammonium formate, 0.1% ammonia solution. Mobile phase B: 94.9% MeCN, 0.1% ammonia solution, 5% mobile phase A.

Gradient program (flow rate 1.2 mL/min, column temperature 40° C.):

| Time | A % | B % |
|------|-----|-----|
| 0.00 | 95.0 | 5.0 |
| 4.00 | 5.0 | 95.0 |
| 5.50 | 5.0 | 95.0 |

Method 8: Gemini C18 30×3.0 mm, 3 μm column. Mobile phase A: 99.9% 10 mM ammonium formate, 0.1% formic acid. Mobile phase B: 100% MeCN.

Gradient program (flow rate 1.2 mL/min, column temperature 40° C.):

| Time | A % | B % |
|------|-----|-----|
| 0.00 | 95.0 | 5.0 |
| 2.30 | 5.0 | 95.0 |
| 3.40 | 5.0 | 95.0 |
| 3.50 | 95.0 | 5.0 |

Method 9: Gemini C18 30×3.0 mm, 3 μm column. Mobile phase A: 99.9% 10 mM ammonium formate, 0.1% ammonia solution. Mobile phase B: 100% MeCN.

Gradient program (flow rate 1.2 mL/min, column temperature 40° C.):

| Time | A % | B % |
|------|-----|-----|
| 0.00 | 95.0 | 5.0 |
| 2.30 | 5.0 | 95.0 |
| 3.40 | 5.0 | 95.0 |
| 3.50 | 95.0 | 5.0 |

Method 10: Luna C18(2) 250×21.2 mm, 5 μm column. Mobile phase A: 99.92% water, 0.08% formic acid. Mobile phase B: 99.92% MeCN, 0.08% formic acid.

Gradient program (flow rate 25.0 mL/min), column temperature: ambient, variable gradient.

Method 11: Luna C18(2) 250×21.2 mm, 5 μm column. Mobile phase A: 10 mM NH$_4$OAc, pH 5.8. Mobile phase B: 95% MeCN, 5% 200 mM NH$_4$OAc, pH 5.8.

Gradient program (flow rate 25.0 mL/min), column temperature: ambient, variable gradient.

Method 12: Gemini C18 150×21.2 mm, 10 μm column. Mobile phase A: 99.9% ammonium formate, 0.1% formic acid. Mobile phase B: 94.9% MeCN, 0.1% formic acid, 5% mobile phase A.

Gradient program (flow rate 20.0 mL/min), column temperature: ambient, variable gradient.

Method 13: Gemini C18 150×21.2 mm, 10 μm column. Mobile phase A: 99.9% ammonium formate, 0.1% ammonia solution. Mobile phase B: 94.9% MeCN, 0.1% ammonia solution, 5% mobile phase A.

Gradient program (flow rate 20.0 mL/min), column temperature: ambient, variable gradient.

Intermediate 1

Ethyl 3-amino-3-methylbutanoate hydrochloride

To a stirred solution of ethyl 3,3-dimethylacrylate (5.0 g, 39.1 mmol) in EtOH (20 mL) in a Parr® reactor at 0° C. was added liquid NH$_3$ (ca 20 mL). The reactor was sealed and heated to 90° C. for 24 h. The reaction mixture was cooled to r.t., bubbled with nitrogen to remove the residual NH$_3$ and treated with 4M HCl in dioxane (10 mL). The reaction mixture was stirred for 30 minutes at r.t. and then evaporated in vacuo to dryness. The resulting grey paste was triturated with DCM, filtered and dried to give the title compound (5.0 g, 70%) as a grey solid that was used without further purification. $\delta_H$ (CDCl$_3$) 8.27 (3H, br. s), 4.10 (2H, q, J 7.1 Hz), 2.65 (2H, s), 1.26 (6H, s), 1.20 (3H, t, J 7.1 Hz).

Intermediate 2

Ethyl 3-[(3-ethoxy-3-oxopropanoyl)amino]-3-methylbutanoate

To a stirred suspension of Intermediate 1 (5.0 g, 27.4 mmol) in DCM (40 mL) was added NEt$_3$ (11.1 g, 15.3 mL, 109.6 mmol). The reaction mixture was then cooled to 0° C. and ethyl malonyl chloride (4.4 g, 3.7 mL, 28.8 mmol) was added dropwise. The suspension was stirred at r.t. for 2 h before it was diluted with DCM (50 mL) and washed with aqueous 1M HCl (50 mL) and water (2×50 mL). The organics were dried over MgSO$_4$, filtered and concentrated in vacuo to give the title compound (5.0 g, 71%) as an orange oil that was used without further purification. $\delta_H$ (DMSO-d$_6$) 7.75 (1H, br. s), 4.15-3.95 (4H, m), 3.14 (2H, s), 2.71 (2H, s), 1.29 (6H, s), 1.21-1.11 (6H, m).

Intermediate 3

6,6-Dimethylpiperidine-2,4-dione

To a stirred solution of NaOEt, prepared in situ from Na (0.53 g, 23.16 mmol) in EtOH (30 mL), was added dropwise a solution of Intermediate 2 (5.00 g, 19.30 mmol) in toluene (30 mL) and the reaction mixture was heated to 80° C. for 2 h. The solution was then concentrated to ca 10 mL and the residue was dissolved in toluene (30 mL) and extracted with water (3×30 mL). The combined aqueous layers were acidified to pH 2-3 with aqueous 1M HCl and extracted with EtOAc (4×50 mL). The combined organic fractions were dried (MgSO$_4$), filtered and evaporated in vacuo to give a pale yellow solid that was dissolved in MeCN (90 mL) containing 1% water. The solution was heated to reflux for 2 h and then evaporated in vacuo to dryness. The resulting solid was triturated with diisopropyl ether, filtered and dried to give the title compound (1.55 g, 57%) as a cream solid that was used without further purification. Both the keto and enol forms were observed (ratio 3.6:1 keto/enol). $\delta_H$ (DMSO-d$_6$) 10.29 (1H, br. s, enol), 8.14 (1H, br. s, keto), 6.66 (1H, s, enol), 4.81 (1H, s, enol), 3.15 (2H, s), 2.51 (2H, s), 1.20 (6H, s, keto), 1.18 (6H, s, enol).

Intermediate 4

(3a,R)-Tetrahydro-3H-[1,2,3]oxathiazolo[4,3-c][1,4]oxazine 1,1-dioxide

To a solution of Intermediate 19 (30 g, 257 mmol) dissolved in anhydrous DCM (250 mL) was added pyridine (43.5 mL, 539 mmol) and the solution was cooled to −70° C. (CO$_2$/IPA bath). Sulphuryl chloride (21.7 mL, 270 mmol) dissolved in anhydrous DCM (200 mL) was added dropwise over 1 h (so as to maintain the reaction temperature below −60° C.). The reaction was stirred at −70° C. for 2 h and at −10 to −20° C. (MeOH/ice bath) for 2 h before being quenched by the addition of water (15 mL) and warming to r.t. The solution was separated and the aqueous fraction extracted with further DCM (2×100 mL). The combined organic fractions were washed with water (15 mL), brine (15 mL), dried (Na$_2$SO$_4$), filtered and concentrated in vacuo to give the title compound (24.7 g, 54%) as a yellow oil which solidified to an orange sticky solid on standing at r.t. that was used without further purification. δ$_H$ (CDCl$_3$) 4.51 (1H, dd, J 8.1 and J 6.4 Hz), 4.23 (1H, dd, J 9.1 and J 8.1 Hz), 3.95 (1H, dd, J 11.6 and J 3.4 Hz), 3.84-3.64 (3H, m), 3.54 (1H, dd, J 11.6 and J 7.7 Hz), 3.29 (1H, dt, J 12.0 and J 3.4 Hz), 3.06 (1H, m).

Intermediate 5

(3S)-3-(Prop-2-yn-1-yl)morpholine

To a solution of trimethylsilyl acetylene (27.59 mL, 195.25 mmol) dissolved in anhydrous THF (250 mL) at 0° C. was added n-butyllithium (78.1 mL, 201 mmol, 2.5M in hexanes) dropwise over 15 minutes. After stirring at this temperature for 40 minutes, a solution of Intermediate 4 (11.65 g, 65.083 mmol) dissolved in DMPU (11 mL) was added slowly over 15 minutes and the reaction mixture was allowed to warm to r.t. After stirring at r.t. for 18 h, the reaction mixture was quenched by the addition of water (ca 4 mL) and the solvent (not DMPU) was removed in vacuo. To the resultant dark oil were added aqueous HCl (10% v/v, 200 mL) and MeOH (100 mL) and the reaction mixture was stirred at r.t. for 18 h. The solution was then concentrated in vacuo to give the title compound (17.059 g, ca 74% yield) as a crude dark oil (containing ca 11 mL DMPU) that was used without further purification. δ$_H$ (CD$_3$OD) 3.89 (1H, dd, J 11.2 and J 3.1 Hz), 3.76 (1H, dt, J 11.2 and J 2.7 Hz), 3.45-3.56 (1H, m), 3.25 (1H, m), 2.89 (3H, m), 2.39 (1H, t, J 2.7 Hz), 2.25 (2H, dd, J 6.8 and J 2.7 Hz). Exchangeable proton was not observed.

Intermediate 6 tert-Butyl (3S)-3-(prop-2-yn-1-yl)morpholine-4-carboxylate

To a solution of crude Intermediate 5 (17.059 g, containing 11 mL DMPU), dissolved in anhydrous DCM (300 mL) at 0° C., was added DIPEA (13.04 mL, 74.85 mmol) and di-tert-butyl dicarbonate (15.624 g, 71.59 mmol) and the reaction mixture warmed to r.t. After stirring for 18 h, the reaction mixture was washed with brine and the organic fraction was dried using an Isolute® phase separator cartridge and concentrated in vacuo to give a dark brown oil. Purification by column chromatography (SiO$_2$, 10:1 EtOAc/hexanes) gave the title compound (8.79 g, 59% from Intermediate 4) as a yellow oil. δ$_H$ (CD$_3$OD) 3.95 (1H, m), 3.75 (1H, d, J 14.2 Hz), 3.70 (1H, m), 3.58 (1H, m), 3.42 (1H, m), 3.30 (1H, m), 2.95 (1H, m), 2.51 (1H, m), 2.37 (1H, m), 2.19 (1H, t, J 2.7 Hz), 1.35 (9H, s).

Intermediate 7

Method H tert-Butyl (3S)-3-[3-(trimethylsilyl)prop-2-yn-1-yl]morpholine-4-carboxylate To a solution of Intermediate 6 (8.05 g, 35.7 mmol) dissolved in anhydrous THF (250 mL) at 0° C. was added n-butyllithium (15.7 mL, 39.3 mmol, 2.5 M in hexanes) dropwise over 15 minutes. After stirring for 30 minutes, chlorotrimethylsilane was added slowly over 5 minutes and the reaction mixture stirred for 45 minutes and then allowed to warm to r.t. After stirring at r.t. for 18 h, the reaction mixture was quenched by the addition of water (ca 1 mL) and the solvent was removed in vacuo. The crude mixture was dissolved in DCM and washed with water, the aqueous phase was extracted with further DCM (500 mL) and the combined organic fractions were dried using an Isolute® phase separator cartridge and concentrated in vacuo to give a dark brown oil. Purification by column chromatography (SiO$_2$, 5-20% EtOAc/hexanes) gave the title compound (8.1 g, 76%) as a colourless oil and recovered starting material (1.25 g, 15%). δ$_H$ (CD$_3$OD) 3.91 (1H, m), 3.82 (1H, d, J 11.7 Hz), 3.70 (1H, dd, J 3.6 and J 11.4 Hz), 3.58 (1H, dd, J 2.9 and J 13.7 Hz), 3.40-3.20 (2H, m), 2.95 (1H, m), 2.60 (1H, dd, J 9.1 and J 16.7 Hz), 2.38 (1H, dd, J 6.4 and J 16.7 Hz), 1.35 (9H, s), 0.00 (9H, s).

Intermediate 8

Method I tert-Butyl (3S)-3-{[5-(difluoromethoxy)-2-(trimethylsilyl)-1H-indol-3-yl]methyl}morpholine-4-carboxylate To a solution of Intermediate 7 (0.571 g, 1.93 mmol) dissolved in DMF (23 mL) was added Intermediate 20 (0.55 g, 1.93 mmol), LiCl (0.082 g, 1.93 mmol), Na$_2$CO$_3$ (0.409 g, 3.86 mmol) and Pd(OAc)$_2$ (0.017 g, 0.08 mmol) and the reaction mixture was degassed under vacuum and then purged with nitrogen. The reaction mixture was then heated at 100° C. for 6 h. The crude reaction mixture was cooled to r.t. and the solvent removed in vacuo to give a brown oil. Purification by column chromatography (SiO$_2$, 10-30% EtOAc/hexanes; followed by SiO$_2$, DCM) gave the title compound (0.462 g, 53%) as a yellow oil. LCMS (ES+) 399.0 ((M-$^t$Bu)+H)$^+$, RT 3.95 minutes (Method 5).

Intermediate 9

Method J 5-(Difluoromethoxy)-3-[(3S)-morpholin-3-ylmethyl]-1H-indole

To Intermediate 8 (0.285 g, 0.63 mmol) at 0° C. was added 4M HCl in 1,4-dioxane (8 mL) and the reaction mixture was stirred at r.t. for 2 h. The reaction mixture was concentrated in vacuo and the crude residue was dissolved in DCM (25 mL) and washed with aqueous sat. NaHCO$_3$ solution (5 mL). The aqueous fraction was further extracted with DCM (3×20 mL) and the combined organic fractions were dried (Na$_2$SO$_4$), filtered and concentrated in vacuo to give the title compound (0.197 g, quantitative) as a yellow oil that was used without further purification. LCMS (ES+) 283.0 (M+H)$^+$, RT 2.27 minutes (Method 5).

Intermediate 10

Method K (3S)-3-{[5-(Difluoromethoxy)-1H-indol-3-yl]methyl}morpholine-4-carbothioamide To a solution of 1,1'-thiocarbonyldiimidazole (0.137 g, 0.77 mmol) in THF (5 mL) was added Intermediate 9 (0.197 g, 0.70 mmol) dissolved in THF (5 mL) and the reaction mixture was stirred at r.t. for 18 h. The reaction mixture was concentrated in vacuo and dissolved in MeCN (7 mL) and aqueous $NH_3$ (20% v/v, 7 mL) added. The reaction mixture was stirred at 60° C. for 4 h. After cooling to r.t., the reaction mixture was concentrated in vacuo to give a yellow oil. The crude material was purified by column chromatography ($SiO_2$, 9:10 EtOAc/hexanes) to give the title compound (0.106 g, 44%) as a yellow oil. LCMS (ES+) 342.0 (M+H)$^+$, RT 2.91 minutes (Method 5).

Intermediate 11

Methyl 3-{[(3S)-4-(tert-butoxycarbonyl)morpholin-3-yl]methyl}-2-(trimethylsilyl)-1H-indole-5-carboxylate The title compound was prepared from methyl 4-amino-3-iodobenzoate and Intermediate 7 according to Method I and was isolated as a yellow sticky solid (59%) after purification by column chromatography ($SiO_2$, 10-25% EtOAc/hexanes). LCMS (ES+) 392.0 ((M-$^t$Bu)+H)$^+$, RT 3.58 minutes (Method 3).

Intermediate 12

Methyl 3-[(3S)-morpholin-3-ylmethyl]-1H-indole-5-carboxylate

The title compound was prepared from Intermediate 11 according to Method J and was isolated as a brown gum (quantitative) that was used as a crude intermediate. LCMS (ES+) 275.0 (M+H)$^+$, RT 2.30 minutes (Method 5).

Intermediate 13

Methyl 3-{[(3S)-4-(aminocarbonothioyl)morpholin-3-yl]methyl}-1H-indole-5-carboxylate The title compound was prepared from Intermediate 12 according to Method K and was isolated as a yellow solid (99%) after purification by column chromatography ($SiO_2$, 0-4% MeOH/DCM). LCMS (ES+) 334.0 (M+H)$^+$, RT 2.25 minutes (Method 4).

Intermediate 14

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxylate To a solution of Intermediate 45 (1.96 g, 4.46 mmol) in DMF (10 mL) and DCM (150 mL) was added pentafluorophenol (0.86 g, 4.68 mmol) and EDC (0.94 g, 4.91 mmol) and the reaction mixture was stirred at r.t. for 16 h. DIPEA (1.15 g, 1.56 mL, 8.92 mmol), and further pentafluorophenol (0.22 g, 1.20 mmol) and EDC (0.24 g, 1.25 mmol), were added and stirred for an additional 2 h at r.t. The reaction mixture was washed with water (2×50 mL), brine (50 mL), dried ($Na_2SO_4$), filtered and concentrated in vacuo. Purification by column chromatography ($SiO_2$, 0-6% MeOH/DCM) gave the title compound (1.41 g, 52%) as a brown gum. LCMS (ES+) 607.3 (M+H)$^+$, RT 3.23 minutes (Method 3).

Intermediate 15

3-Bromo-6,6-dimethylpiperidine-2,4-dione

To a stirred suspension of Intermediate 3 (10.00 g, 70.9 mmol) in THF (200 mL) was added $NaHSO_4$ (2.12 g, 17.7 mmol). The suspension was cooled to 0° C. and NBS (12.62 g, 70.9 mmol) was added portionwise. The reaction mixture was stirred at r.t. for 5 h then DCM (200 mL) and water (100 mL) were added. The aqueous fraction was extracted with DCM (2×100 mL). The combined organic fractions were washed with water (3×200 mL), dried ($Na_2SO_4$), filtered and the solvent evaporated in vacuo. The white solid was triturated with IPA (3×50 mL), then filtered to give the title compound (10.3 g, 66%) as a white solid. $\delta_H$ (DMSO-$d_6$) 10.80 (1H, br. s), 7.26 (1H, br. s), 2.50 (2H, s) for the main tautomer. LCMS (ES+) 220.0 and 222.0 (1:1 ratio) (M+H)$^+$, RT 1.94 minutes (Method 3).

Intermediate 16

N-Benzyl-D-serine

To a stirred solution of D-serine (14.7 g, 140.0 mmol) in aqueous 2M NaOH (70 mL) was added benzaldehyde (14.6 g, 14.0 mL, 138.0 mmol). The reaction mixture was then stirred at r.t. for 1 h before cooling to 5° C. $NaBH_4$ (1.5 g, 40.0 mmol) was added portionwise such that an internal temperature of between 6 and 10° C. was maintained. After addition, the reaction mixture was allowed to stir at 5° C. for 30 minutes and then at r.t. for 1 h. The reaction mixture was cooled to 5° C. and a further portion of $NaBH_4$ (1.5 g, 40.0 mmol) was added portionwise such that an internal temperature of <10° C. was maintained. The ice bath was removed on completion of addition and the reaction mixture stirred at r.t. for 16 h. The reaction mixture was then extracted with $Et_2O$ (3×100 mL) and the aqueous phase acidified to pH 5 with conc. HCl. The resultant white precipitate was filtered and washed with water. The product was dried in vacuo to give the title compound (24.0 g, 88%) as a white solid. $\delta_H$ (DMSO-$d_6$) 7.45-7.30 (5H, m), 4.04-3.91 (2H, m), 3.70-3.61 (3H, m), 3.17 (1H, t, J 5.8 Hz).

Intermediate 17

(3R)-4-Benzyl-5-oxomorpholine-3-carboxylic acid

To a stirred solution of Intermediate 16 (35.0 g, 179.0 mmol) in aqueous NaOH solution (9.3 g, 200.0 mL, 232.5 mmol) at 0° C. was slowly added chloroacetyl chloride (24.2 g, 17.0 mL, 214.0 mmol). The reaction mixture was allowed to warm to r.t. and then stirred for 30 minutes. Aqueous 10M NaOH solution (45.0 mL, 465.0 mmol) was added and the reaction mixture heated to 45° C. for 4 h. The reaction mixture was then cooled to 10° C. and acidified to pH 1 with conc. HCl. On standing at 4° C. the product crystallised from the mixture and was collected by filtration, washed with cold water and then dried in vacuo to give the title compound (18.0 g, 43%) as a white solid. $\delta_H$ (DMSO-$d_6$) 13.51-12.53 (1H, br. s), 7.38-7.25 (5H, m), 5.27 (1H, d, J 15.3 Hz), 4.24-4.10 (3H, m), 3.94-3.88 (2H, m), 3.83 (1H, d, J 15.3 Hz). LCMS (ES+) 236.0 (M+H)$^+$.

Intermediate 18

[(3S)-(4-Benzylmorpholin-3-yl)]methanol

To a stirred solution of Intermediate 17 (17.7 g, 75.3 mmol) in THF (300 mL) was added $NEt_3$ (7.3 g, 10.0 mL, 72.0 mmol). The solution was then cooled to 0° C. and $BH_3.Me_2S$ complex (10M in THF, 45.0 mL, 450.0 mmol) was added slowly. The reaction mixture was heated at reflux for 12 h and, after cooling to r.t., the excess borane was destroyed by slow addition of MeOH at 0° C. The reaction mixture was concentrated in vacuo and the resultant white solid was dissolved in EtOAc (120 mL) and washed with aqueous NaOH solution (20% v/v, 2×100 mL). The organic fraction was then extracted into aqueous 2M HCl (2×150 mL). The combined acidic aqueous fractions were then basified to pH 14 (addition of solid NaOH) and were re-extracted with EtOAc (2×150 mL). The combined organic fractions were washed with brine (150 mL), dried (MgSO$_4$), filtered and concentrated in vacuo to give the title compound (13.5 g, 87%) as a clear oil that required no further purification. $\delta_H$ (CDCl$_3$) 7.29-7.16 (5H, m), 4.05 (1H, d, J 12.8 Hz), 3.88 (1H, dd, J 11.5 and J 4.5 Hz), 3.78 (1H, m), 3.70-3.53 (2H, m), 3.51-3.40 (2H, m), 3.20 (1H, d, J 13.2 Hz), 2.68 (1H, dt, J 12.1 and J 2.8 Hz), 2.48 (1H, m), 2.27 (1H, m), 2.20-2.15 (1H, br. s).

Intermediate 19

(3S)-Morpholin-3-ylmethanol

To a nitrogen-flushed solution of Intermediate 18 (10.0 g, 48.3 mmol) in MeOH (300 mL) was added 10 wt % palladium on carbon (2.0 g) and the reaction mixture placed in a Parr® apparatus under 50 psi of H$_2$ for 18 h. The resulting mixture was then filtered through Celite® and concentrated in vacuo to give the title compound (5.2 g, 92%) as a colourless oil. $\delta_H$ (CDCl$_3$) 3.81-3.76 (2H, m), 3.58-3.43 (3H, m), 3.35-3.28 (1H, m), 2.99-2.91 (5H, br. m). LCMS (ES+) 118.0 (M+H)$^+$.

Intermediate 20

2-Iodo-4-difluoromethoxyaniline

A solution of 4-(difluoromethoxy)aniline (1.0 g, 6.30 mmol) in AcOH (6 mL) was heated to 60° C. and iodine monochloride (1.07 g, 6.6 mmol) in AcOH (15 mL) was added dropwise. The reaction mixture was then heated to 85° C. and stirred for 1.5 h. The reaction mixture was cooled to r.t. and poured into cold water and the resulting suspension filtered. The filtrate was concentrated in vacuo to give a dark brown oil. Purification by column chromatography (SiO$_2$, 10-20% EtOAc/hexanes) gave the title compound (0.40 g, 22%) as a dark brown oil. $\delta_H$ (DMSO-d$_6$) 7.38 (1H, d, J 2.7 Hz), 6.98-6.94 (1H, m), 6.97 (1H, t, J 74.8 Hz), 6.75 (1H, d, J 8.8 Hz), 5.20 (2H, br. s). LCMS (ES+) 286.0 (M+H)$^+$, RT 3.28 minutes (Method 5).

Intermediate 21

Methyl 3-{[(3S)-4-(tert-butoxycarbonyl)morpholin-3-yl]methyl}-1-methyl-2-(trimethylsilyl)-1H-indole-5-carboxylate To a stirred solution of Intermediate 11 (2.0 g, 4.48 mmol) in THF (30 mL) at 0° C. was added NaH (0.19 g, 60% dispersion in oil, 4.93 mmol). The reaction mixture was stirred at this temperature for 30 minutes. Methyl iodide (0.33 mL, 5.37 mmol) was then added, and the reaction mixture allowed to warm to r.t., then stirred for 18 h. Water (1 mL) was added, and the reaction mixture concentrated in vacuo. DCM (25 mL) and water (10 mL) were added. The organic fraction was separated, washed with brine (10 mL), dried (Na$_2$SO$_4$), filtered and concentrated in vacuo. Purification by column chromatography (SiO$_2$, 10-25% EtOAc/hexanes) gave the title compound (1.95 g, 95%) as a pale yellow oil. LCMS (ES+) 405.1 ((M-$^t$Bu)+H)$^+$, RT 3.80 minutes (Method 3).

Intermediate 22

Methyl 1-methyl-3-[(3S)-morpholin-3-ylmethyl]-1H-indole-5-carboxylate

To a stirred solution of Intermediate 21 (1.95 g, 4.23 mmol) in MeOH (15 mL) was added 4M HCl in 1,4-dioxane (20 mL). The reaction mixture was stirred at r.t. for 16 h, then concentrated in vacuo. Water (10 mL) and DCM (10 mL) were added. The aqueous fraction was separated, basified by the addition of aqueous sat. NaHCO$_3$, then extracted with DCM (5×30 mL). The combined organic fractions were dried (Na$_2$SO$_4$), filtered and concentrated in vacuo to give the title compound (1.02 g, 84%) as a yellow solid that was used without further purification. LCMS (ES+) 289.2 (M+H)$^+$, RT 2.00 minutes (Method 3).

Intermediate 23

Methyl 3-{[(3S)-4-(aminocarbonothioyl)morpholin-3-yl]methyl}-1-methyl-1H-indole-5-carboxylate The title compound was prepared from Intermediate 22 according to Method K and was isolated as a brown gum (80%) after purification by column chromatography (SiO$_2$, 0-6% MeOH/DCM). LCMS (ES+) 348.2 (M+H)$^+$, RT 2.63 minutes (Method 3).

Intermediate 24

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1-methyl-1H-indole-5-carboxylate To a stirred solution of Example 2 (1.0 g, 2.20 mmol) in DMF (20 mL) was added pentafluorophenol (0.49 g, 2.64 mmol), DIPEA (0.77 mL, 4.41 mmol) and EDC (0.55 g, 2.86 mmol). The reaction mixture was stirred at r.t. for 16 h, then concentrated in vacuo. DCM (15 mL) and water (15 mL) were added. The organic fraction was separated, dried (Na$_2$SO$_4$), filtered and concentrated in vacuo. Purification by column chromatography (SiO$_2$, 0-4% MeOH/DCM) gave the title compound (1.04 g, 76%) as a yellow gum. LCMS (ES+) 621.3 (M+H)$^+$, RT 3.52 minutes (Method 4).

Intermediate 25 tert-Butyl (3S)-3-{[5-cyano-2-(trimethylsilyl)-1H-indol-3-yl]methyl}morpholine-4-carboxylate The title compound was prepared from Intermediate 7 and 4-amino-3-iodobenzonitrile according to Method I and was isolated as a yellow solid (50%) after work-up (EtOAc and water) and purification by column chromatography (SiO$_2$, 5-100% EtOAc/hexanes). LCMS (ES+) 414.0 (M+H)$^+$, RT 3.92 minutes (Method 5).

Intermediates 26 and 27

(3S)-3-[3-(Trimethylsilyl)prop-2-yn-1-yl]morpholine-4-carbothioamide and (3S)-3-(Prop-2-yn-1-yl)morpholine-4-carbothioamide respectively To a stirred solution of trimethylsilyl acetylene (30.3 mL, 215.0 mmol) in THF (300 mL) at 0° C. was added n-butyllithium (86.2 mL, 2.5M in hexanes, 215.0 mmol) dropwise over 15 minutes. After stirring at this temperature for 30 minutes, Intermediate 4 (19.3 g, 107.7 mmol) was added over 5 minutes. The reaction mixture was stirred at 0° C. for 20 minutes, and then allowed to warm to r.t. After stirring at r.t. for 40 minutes, the reaction mixture was quenched by the addition of 2M aqueous HCl (80 mL) and MeOH (50 mL), then stirred at r.t. for 3 h. The reaction mixture was concentrated in vacuo. The residue was dissolved in THF (60 mL). DIPEA (4.9 mL, 28.4 mmol) then 1,1'-thiocarbonyldiimidazole (5.3 g, 29.7 mmol) were added. The reaction mixture was stirred at r.t. for 16 h, then partitioned between DCM (50 mL) and water (30 mL). The organic fraction was dried ($Na_2SO_4$), filtered and concentrated in vacuo. Purification by column chromatography ($SiO_2$, 0-2% MeOH/DCM, followed by $SiO_2$, 60-80% EtOAc/hexanes) gave the first title compound (2.35 g, 34%) as a brown gum, LCMS (ES+) 257.0 $(M+H)^+$, RT 3.206 minutes (Method 5), followed by the second title compound (1.55 g, 31%) as a brown gum, LCMS (ES+) 185.0 $(M+H)^+$, RT 2.47 minutes (Method 5). They were both used individually without further purification.

Intermediate 28

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-2-(trimethylsilyl)-1-benzofuran-5-carboxylate The title compound was prepared from Intermediate 49 and methyl 4-hydroxy-3-iodobenzoate according to Method I and was isolated as a brown gum (49%) after purification by column chromatography ($SiO_2$, 60-100% EtOAc/hexanes). LCMS (ES+) 528.2 $(M+H)^+$, RT 3.46 minutes (Method 9).

Intermediate 29

3-{[(3S)-4-(6,6-Dimethyl-4-oxo-4,5,6,7-tetrahydro[1,3]thiazolo[5,4-c]pyridin-2-yl)morpholin-3-yl]methyl}-1-benzofuran-5-carboxylic acid To a stirred solution of Intermediate 28 (0.326 g, 0.62 mmol) in 1,4-dioxane (8 mL) was added a solution of $LiOH.H_2O$ (0.054 g, 1.29 mmol) in water (5 mL). The reaction mixture was stirred at r.t. for 1 h, then at 60° C. for 1 h, and then at r.t. for 18 h before being concentrated in vacuo. The residue was dissolved in water (20 mL) and the solution washed with DCM (3×25 mL). The aqueous fraction was separated, acidified with 1M aqueous HCl, then extracted with EtOAc (4×50 mL). The combined organic fractions were dried ($Na_2SO_4$), filtered and concentrated in vacuo to give the title compound (0.135 g, 49%) as an off-white solid that was used without further purification. LCMS (ES+) 442.2 $(M+H)^+$, RT 1.82 minutes (Method 9).

Intermediate 30

Pentafluorophenyl 3-{[(3S)-4-(6,6-dimethyl-4-oxo-4,5,6,7-tetrahydro[1,3]thiazolo[5,4-c]pyridin-2-yl)morpholin-3-yl]methyl}-1-benzofuran-5-carboxylate To a stirred solution of Intermediate 29 (0.135 g, 0.31 mmol) in DMF (8 mL) was added pentafluorophenol (0.062 g, 0.34 mmol) and EDC (0.070 g, 0.37 mmol). The reaction mixture was stirred at r.t. for 16 h, then used as such for the next step. LCMS (ES+) 608.1 $(M+H)^+$, RT 3.39 minutes (Method 9).

Intermediate 31 tert-Butyl (3S)-3-{[5-cyano-1-methyl-2-(trimethylsilyl)-1H-indol-3-yl]methyl}morpholine-4-carboxylate To a stirred solution of Intermediate 25 (1.6 g, 3.87 mmol) in THF (20 mL) at −78° C. was added n-butyllithium (1.9 mL, 2.5M in THF, 4.85 mmol). After stirring at this temperature for 10 minutes, MeI (0.3 mL, 4.84 mmol) was added, and the reaction mixture warmed to r.t. over 1 h. EtOAc (10 mL) and brine (20 mL) were added. The aqueous fraction was separated and extracted with EtOAc (3×20 mL). The combined organic fractions were dried ($Na_2SO_4$), filtered and evaporated in vacuo. Purification by column chromatography ($SiO_2$, 15-60% EtOAc/hexanes) gave the title compound (1.60 g, quantitative) as an off-white solid. LCMS (ES+) 427.0 $(M+H)^+$, RT 2.51 minutes (Method 12).

Intermediate 32

1-Methyl-3-[(3S)-morpholin-3-ylmethyl]-1H-indole-5-carbonitrile

The title compound was prepared from Intermediate 31 according to Method J and was isolated as a yellow oil (71%) that was used without further purification. LC, RT 1.45 minutes (Method 12).

Intermediate 33

(3S)-3-[(5-Cyano-1-methyl-1H-indol-3-yl)methyl]morpholine-4-carbothioamide

The title compound was prepared from Intermediate 32 according to Method K and was isolated as a brown solid (92%) that was used without further purification. LCMS (ES+) 298.0 $(M-NH_2)^+$, RT 1.76 minutes (Method 12).

Intermediate 34 tert-Butyl (3S)-3-{[2-(trimethylsilyl)-1H-indol-3-yl]methyl}morpholine-4-carboxylate The title compound was prepared from Intermediate 7 and 2-iodoaniline according to Method I and was isolated as a white solid (40%) after purification by column chromatography ($SiO_2$, 15-60% EtOAc/hexanes). LCMS (ES+) 333.0 $((M-^tBu)+H)^+$, 2.50 minutes (Method 12).

Intermediate 35 tert-Butyl (3S)-3-{[1-methyl-2-(trimethylsilyl)-1H-indol-3-yl]methyl}morpholine-4-carboxylate The title compound was prepared from Intermediate 34 according to Method W (using only 1.1 equivalent of NaH, doing the work-up in EtOAc and water, and drying the separated organic fraction with $Na_2SO_4$) and was isolated as a yellow oil (24%) after purification by column chromatography ($SiO_2$, 15-60% EtOAc/hexanes). $\delta_H$ (DMSO-$d_6$) 7.90-7.60 (1H, br. s), 7.39 (1H, d, J 8.3 Hz), 7.25-7.10 (1H, m), 7.10-7.00 (1H, m), 4.07-4.05 (1H, m), 3.88-3.85 (1H, m), 3.80 (3H, s), 3.70-3.60 (1H, br. s), 3.48-3.39 (2H, m), 3.31-3.24 (1H, m), 3.24-3.22 (2H, m), 2.90-2.75 (1H, m), 1.38 (9H, s), 0.47 (9H, s). LCMS (ES+) 403.0 $(M+H)^+$, 347.0 $((M-^tBu)+H)$, RT 2.66 minutes (Method 12).

Intermediate 36

1-Methyl-3-[(3S)-morpholin-3-ylmethyl]-1H-indole

The title compound was prepared from Intermediate 35 according to Method J and was isolated as a colourless oil (88%) that was used without further purification. LCMS (ES+) 230.0 (M+H)$^+$, RT 1.53 minutes (Method 12).

Intermediate 37

(3S)-3-[(1-Methyl-1H-indol-3-yl)methyl]morpholine-4-carbothioamide

The title compound was prepared from Intermediate 36 according to Method K and was isolated as a yellow solid (48%) that was used without further purification. LCMS (ES+) 290.0 (M+H)$^+$, RT 1.66 minutes (Method 12).

Intermediate 38

6,6-Dimethyl-2-[(3S)-3-{[2-(trimethylsilyl)-1-benzofuran-3-yl]methyl}morpholin-4-yl]-6,7-dihydro[1,3]thiazolo[5,4-c]pyridin-4(5H)-one The title compound was prepared from Intermediate 49 and 2-iodophenol according to Method I and was isolated as a yellow oil (77%) after purification by column chromatography (SiO$_2$, 0-50% EtOAc/hexanes). $\delta_H$ (CDCl$_3$) 7.84-7.81 (1H, m), 7.27-7.25 (1H, m), 7.11-7.07 (2H, m), 5.00-4.90 (1H, m), 4.30-4.20 (1H, m), 4.00-3.86 (1H, m), 3.60-3.20 (7H, m), 1.41 (2H, s), 1.98-1.20 (6H, m), 0.22 (9H, s).

Intermediate 39

4-Hydroxy-3-iodobenzaldehyde

To a stirred solution of 4-hydroxybenzaldehyde (2.0 g, 16.39 mmol) in AcOH (30 mL) was added N-iodosuccinimide (4.5 g, 19.67 mmol). The reaction mixture was stirred at r.t. for 16 h, then filtered. The filtrate was poured onto water (100 mL) and EtOAc (50 mL) was added. The aqueous fraction was separated, then extracted with EtOAc (3×50 mL). The combined organic fractions were washed with water (2×20 mL), dried (Na$_2$SO$_4$), filtered and concentrated in vacuo to give the title compound (2.0 g, 50%) as a white solid that was used without further purification. LCMS (ES–) 247.1 (M–H)$^-$, RT 1.44 minutes (Method 9).

Intermediate 40

4-Hydroxy-3-iodobenzonitrile

To a stirred solution of Intermediate 39 (5.2 g, 20.97 mmol) in formic acid (60 mL) was added sodium acetate (2.1 g, 25.16 mmol), followed by hydroxylamine hydrochloride (8.7 g, 125.8 mmol). The reaction mixture was stirred at 105° C. for 3 h, then cooled to r.t. and poured onto water. The solid formed was filtered to give the title compound (3.0 g, 58%) as a white solid that was used without further purification. LCMS (ES+) 246.1 (M+H)$^+$, RT 1.64 minutes (Method 11).

Intermediate 41

3-[(3S)-Morpholin-3-ylmethyl]-1-benzofuran-5-carbonitrile

The title compound was prepared from Intermediate 7 and Intermediate 40 according to Method I, followed by Method J then Method AI, and was isolated as a yellow solid (10%) after purification by column chromatography (SiO$_2$, 0-10% MeOH/DCM). LCMS (ES+) 243.1 (M+H)$^+$, RT 1.41 minutes (Method 12).

Intermediate 42

(3S)-3-[(5-Cyano-1-benzofuran-3-yl)methyl]morpholine-4-carbothioamide

The title compound was prepared from Intermediate 41 according to Method K and was isolated as a yellow solid (quantitative) that was used without further purification. LCMS (ES+) 302.1 (M+H$^+$), RT 1.54 minutes (Method 12).

Intermediate 43

Method N

2-[(3S)-3-{[5-(Difluoromethoxy)-1H-indol-3-yl]methyl}morpholin-4-yl]-6,6-dimethyl-6,7-dihydro[1,3]thiazolo[5,4-c]pyridin-4(5H)-one To a solution of Intermediate 10 (0.07 g, 0.21 mmol) in THF (3 mL) was added Intermediate 15 (0.048 g, 0.22 mmol) and DIPEA (0.059 mL, 0.41 mmol) and the reaction mixture was stirred at 60° C. for 1.5 h. The reaction mixture was concentrated in vacuo to give a yellow oil. Purification by column chromatography (SiO$_2$, 1-2% MeOH/DCM; followed by SiO$_2$, 80-100% EtOAc/DCM) and freeze-drying (MeCN/water) gave the title compound (0.019 g, 20%) as an off-white solid. $\delta_H$ (CD$_3$OD) 7.73 (1H, d, J 2.1 Hz), 7.32 (1H, d, J 8.7 Hz), 7.20 (1H, s), 6.93 (1H, dd, J 8.7 and J 2.3 Hz), 6.72 (1H, t, J 75.6 Hz), 4.38-4.30 (1H, m), 4.09-4.06 (1H, m), 3.90 (1H, d, J 11.8 Hz), 3.71-3.46 (4H, m), 3.40-3.31 (1H, m), 3.10-3.04 (1H, m), 2.83 (2H, s), 1.36 (6H, s). Exchangeable protons were not observed. LCMS (ES+) 463.0 (M+H)$^+$, RT 3.07 minutes (Method 5).

Intermediate 44

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1H-indole-5-carboxylate The title compound was prepared from Intermediate 13 and Intermediate 15 according to Method N and was isolated as a yellow solid (69%) after purification by column chromatography (SiO$_2$, 0-5% MeOH/DCM). $\delta_H$ (CD$_3$OD) 8.62 (1H, d, J 1.0 Hz), 7.81 (1H, dd, J 8.6 and J 1.6 Hz), 7.39 (1H, d, J 8.6 Hz), 7.24 (1H, s), 4.37 (1H, m), 4.07 (1H, m), 3.95 (3H, s), 3.90 (1H, d, J 11.7 Hz), 3.73-3.52 (4H, m), 3.38 (1H, m), 3.18 (1H, dd, J 13.9 and J 5.4 Hz), 2.87 (1H, d, J 16.9 Hz), 2.81 (1H, d, J 16.9 Hz), 1.37 (3H, s), 1.36 (3H, s). Exchangeable protons were not observed. LCMS (ES+) 455.0 (M+H)$^+$, RT 2.59 minutes (Method 4).

Intermediate 45

3-{[(3S)-4-(6,6-Dimethyl-4-oxo-4,5,6,7-tetrahydro[1,3]thiazolo[5,4-c]pyridin-2-yl)morpholin-3-yl]methyl}-1H-indole-5-carboxylic acid To Intermediate 44 (2.18 g, 4.80 mmol) dissolved in 1,4-dioxane (20 mL) was added a solution of LiOH.H$_2$O (0.40 g, 9.60 mmol) in water (20 mL) and the reaction mixture stirred at r.t. for 16 h. Further LiOH.H$_2$O (0.10 g, 2.40 mmol) in water (5 mL) was added and the reaction mixture stirred at 50° C. for 3 h. The reaction mixture was concentrated in vacuo and the crude residue was partitioned between water (100 mL) and DCM (200 mL). The aqueous phase was acidified to pH 1 by the addition of aqueous HCl (10% v/v) and extracted with EtOAc (3×200 mL) and the combined organic fractions were concentrated in vacuo to give the title compound (2.37 g, quantitative) as a yellow solid. $\delta_H$ (DMSO-$d_6$) 12.35 (1H, br. s), 11.23 (1H, s), 8.58 (1H, s), 7.71 (1H, dd, J 8.6 and J 1.5 Hz), 7.38 (1H, d, J 8.6 Hz), 7.30 (1H, d, J 2.1 Hz), 7.27 (1H, s), 4.27 (1H, m), 3.98 (1H, m), 3.73 (1H, d, J 11.6 Hz), 3.62-3.43 (4H, m), 3.28 (1H, m), 2.96 (1H, dd, J 13.9 and J 3.9 Hz), 2.83 (1H, d, J 16.9 Hz), 2.76 (1H, d, J 16.9 Hz), 1.26 (6H, s). LCMS (ES+) 441.0 (M+H)$^+$, RT 2.65 minutes (Method 5).

Intermediate 46

Method O 6,6-Dimethyl-2-[(3S)-3-{[5-(piperidin-1-ylcarbonyl)-1H-indol-3-yl]methyl}morpholin-4-yl]-6,7-dihydro[1,3]thiazolo[5,4-c]pyridin-4(5H)-one To Intermediate 14 (0.206 g, 0.34 mmol) dissolved in DCM (5 mL) was added piperidine (0.035 g, 0.04 mL, 0.409 mmol) and the reaction mixture stirred at r.t. for 1 h. The reaction mixture was concentrated in vacuo and the crude residue was purified by column chromatography (SiO$_2$, 0-5% MeOH/DCM). The sample was freeze-dried (MeCN/water) to give the title compound (0.086 g, 50%) as a white powder. $\delta_H$ (DMSO-$d_6$) 11.07 (1H, s), 7.91 (1H, s), 7.36 (1H, d, J 8.3 Hz), 7.29 (1H, s), 7.27 (1H, d, J 1.9 Hz), 7.10 (1H, dd, J 8.5 and J 1.3 Hz), 4.19 (1H, m), 3.98 (1H, d, J 6.0 Hz), 3.74 (1H, d, J 11.7 Hz), 3.57 (4H, br. s), 3.50 (4H, m), 3.36-3.22 (1H, m), 2.92 (1H, dd, J 13.9 and J 4.1 Hz), 2.71 (2H, t, J 17.1 Hz), 1.66-1.49 (6H, m), 1.26 (6H, s). LCMS (ES+) 508.0 (M+H)$^+$, RT 2.88 minutes (Method 5).

Intermediate 47

3-{[(3S)-4-(6,6-Dimethyl-4-oxo-4,5,6,7-tetrahydro[1,3]thiazolo[5,4-c]pyridin-2-yl)morpholin-3-yl]methyl}-N,N-dimethyl-1H-indole-5-carboxamide The title compound was prepared from Intermediate 14 and dimethylamine according to Method O and was isolated as a white powder (70%) after purification by column chromatography (SiO$_2$, 0-10% MeOH/DCM) and freeze-drying (MeCN/water). $\delta_H$ (CD$_3$OD) 8.08 (1H, d, J 0.9 Hz), 7.41 (1H, dd, J 8.3 and J 0.6 Hz), 7.24 (1H, s), 7.21 (1H, dd, J 8.5 and J 1.7 Hz), 4.35 (1H, m), 4.07 (1H, m), 3.89 (1H, d, J 11.7 Hz), 3.76-3.54 (4H, m), 3.42 (1H, dd, J 13.9 and J 10.2 Hz), 3.18-3.05 (7H, m), 2.82 (2H, s), 1.38 (6H, s). Exchangeable protons were not observed. LCMS (ES+) 468.5 (M+H)$^+$, RT 2.36 minutes (Method 3).

Intermediate 48

Method W

N,N,1-Trimethyl-3-{[(3S)-4-(5,6,6-trimethyl-4-oxo-4,5,6,7-tetrahydro[1,3]thiazolo[5,4-c]pyridin-2-yl)morpholin-3-yl]methyl}-1H-indole-5-carboxamide To a stirred solution of Intermediate 47 (0.103 g, 0.22 mmol) in DMF (5 mL) was added NaH (0.019 g, 60% dispersion in oil, 0.48 mmol) and the reaction mixture was stirred at r.t. for 10 minutes. Methyl iodide (0.34 mL, 0.55 mmol) was added. The reaction mixture was stirred at r.t. for 2 h, then quenched with the addition of water (0.5 mL) and concentrated in vacuo. DCM (20 mL) and water (20 mL) were added. The organic fraction was separated via an Isolute® phase separation cartridge and concentrated in vacuo. Purification by column chromatography (SiO$_2$, 0-3% MeOH/DCM) gave the title compound (0.085 g, 78%) as a white solid. $\delta_H$ (CD$_3$OD) 8.08 (1H, d, J 0.9 Hz), 7.41 (1H, d, J 8.5 Hz), 7.27 (1H, dd, J 8.5 and 1.5 Hz), 7.18 (1H, s), 4.38-4.27 (1H, m), 4.13-4.00 (1H, m), 3.88 (1H, d, J 11.8 Hz), 3.80 (3H, s), 3.73-3.52 (4H, m), 3.46-3.34 (1H, m), 3.23-3.02 (7H, m), 2.99 (3H, s), 2.87 (2H, s), 1.40 (3H, s), 1.39 (3H, s). LCMS (ES+) 496.3 (M+H)$^+$, RT 2.45 minutes (Method 3).

Intermediate 49

6,6-Dimethyl-2-{(3S)-3-[3-(trimethylsilyl)prop-2-yn-1-yl]morpholin-4-yl}-6,7-dihydro[1,3]thiazolo[5,4-c]pyridin-4(5H)-one The title compound was prepared from Intermediate 15 and Intermediate 26 according to Method N and was isolated as a yellow solid (70%) after purification by column chromatography (SiO$_2$, 60-80% EtOAc/hexanes). A portion (0.10 g) of this material was further purified by column chromatography (SiO$_2$, 0-2% MeOH/DCM) to give the title compound (0.06 g) as a white solid. $\delta_H$ (CD$_3$OD) 4.22-4.08 (1H, m), 4.02-3.83 (2H, m), 3.71-3.50 (3H, m), 3.49-3.33 (1H, m), 2.76-2.66 (4H, m), 1.29 (3H, s), 1.28 (3H, s), 0.00 (9H, s). Exchangeable proton was not observed. LCMS (ES+) 378.2 (M+H)$^+$, RT 2.86 minutes (Method 4).

Example 1

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1-methyl-1H-indole-5-carboxylate The title compound was prepared from Intermediate 23 and Intermediate 15 according to Method N and was isolated as a white solid (91%) after purification by column chromatography (SiO$_2$, 0-4% MeOH/DCM, followed by SiO$_2$, 0-2% MeOH/EtOAc), then preparative HPLC (Method 13). $\delta_H$ (CD$_3$OD) 8.62-8.59 (1H, m), 7.86 (1H, dd, J 8.7 and 1.6 Hz), 7.41-7.35 (1H, m), 7.18 (1H, s), 4.41-4.31 (1H, m), 4.13-4.02 (1H, m), 3.95 (3H, s), 3.90 (1H, d, J 11.8 Hz), 3.79 (3H, s), 3.76-3.55 (4H, m), 3.44-3.36 (1H, m), 3.15 (1H, dd, J 13.9 and 5.4 Hz), 2.85 (1H, d, J 16.9 Hz), 2.80 (1H, d, J 16.9 Hz), 1.36 (3H, s), 1.35 (3H, s). Exchangeable proton was not observed. LCMS (ES+) 469.3 (M+H)$^+$, RT 2.88 minutes (Method 4).

Example 2

3-{[(3S)-4-(6,6-Dimethyl-4-oxo-4,5,6,7-tetrahydro[1,3]thiazolo[5,4-c]pyridin-2-yl)morpholin-3-yl]methyl}-1-methyl-1H-indole-5-carboxylic acid To a stirred suspension of Example 1 (1.15 g, 2.46 mmol) in 1,4-dioxane (20 mL) and MeOH (5 mL) was added a solution of LiOH.H$_2$O (0.21 g, 4.91 mmol) in water (5 mL). The reaction mixture was stirred at 60° C. for 16 h, then concentrated in vacuo. Water (100 mL) and DCM (200 mL) were added. The aqueous fraction was separated, acidified to pH 1 by the addition of 1M aqueous HCl, then extracted with EtOAc (4×200 mL). The combined organic fractions were dried (Na$_2$SO$_4$), filtered and concentrated in vacuo. The solid was washed with EtOAc to give the title compound (1.0 g, 90%) as a white solid. $\delta_H$ (CD$_3$OD) 8.64 (1H, d, J 1.1 Hz), 7.88 (1H, dd, J 8.7 and 1.5 Hz), 7.36 (1H, d, J 8.7 Hz), 7.15 (1H, s), 4.52-4.39 (1H, m), 4.12-4.02 (1H, m), 3.91 (1H, d, J 11.7 Hz), 3.79 (3H, s), 3.76-3.65 (2H, m), 3.64-3.50 (2H, m), 3.44-3.34 (1H, m), 3.16 (1H, dd, J 13.9 and 5.3 Hz), 2.87 (1H, d, J 17.0 Hz), 2.81 (1H, d, J 17.0 Hz), 1.36 (3H, s), 1.35 (3H, s). Exchangeable protons were not observed. LCMS (ES+) 455.2 (M+H)$^+$, RT 2.57 minutes (Method 3).

Example 3

3-{[(3S)-4-(6,6-Dimethyl-4-oxo-4,5,6,7-tetrahydro[1,3]thiazolo[5,4-c]pyridin-2-yl)-morpholin-3-yl]methyl}-N,1-dimethyl-N-(2-methoxyethyl)-1H-indole-5-carboxamide The title compound was prepared from Intermediate 24 and N-(2-methoxyethyl)-methylamine according to Method O and was isolated as a white solid (70%) after purification by column chromatography (SiO$_2$, 0-6% MeOH/DCM). $\delta_H$ (CD$_3$OD) 8.09 (1H, br. s), 7.40 (1H, d, J 8.4 Hz), 7.26 (1H, dd, J 8.4 and 1.4 Hz), 7.17 (1H, s), 4.42-4.32 (1H, m), 4.13-4.02 (1H, m), 3.89 (1H, d, J 11.7 Hz), 3.79 (3H, s), 3.74-3.25 (12H, m), 3.16 (3H, s), 3.14-3.04 (1H, m), 2.81 (2H, s), 1.37 (6H, s). Exchangeable proton was not observed. LCMS (ES+) 526.3 (M+H)$^+$, RT 2.58 minutes (Method 3).

Example 4

N-(Cyanomethyl)-3-{[(3S)-4-(6,6-dimethyl-4-oxo-4,5,6,7-tetrahydro[1,3]thiazolo[5,4-c]pyridin-2-yl)morpholin-3-yl]methyl}-N,1-dimethyl-1H-indole-5-carboxamide The title compound was prepared from Intermediate 24 and (methylamino)-acetonitrile hydrochloride according to Method O (with the addition of 1.2 equivalents of DIPEA) and was isolated as a white solid (63%) after purification by column chromatography (SiO$_2$, 0-6% MeOH/DCM). $\delta_H$ (CD$_3$OD) 8.17 (1H, d, J 0.9 Hz), 7.44 (1H, d, J 8.6 Hz), 7.34 (1H, dd, J 8.6 and 1.5 Hz), 7.20 (1H, s), 4.59 (1H, d, J 17.3 Hz), 4.51 (1H, d, J 17.3 Hz), 4.41-4.30 (1H, m), 4.11-4.01 (1H, m), 3.88 (1H, d, J 11.7 Hz), 3.80 (3H, s), 3.75-3.50 (4H, m), 3.45-3.33 (1H, m), 3.24 (3H, s), 3.11 (1H, dd, J 13.9 and 4.9 Hz), 2.81 (2H, s), 1.37 (3H, s), 1.36 (3H, s). Exchangeable proton was not observed. LCMS (ES+) 507.2 (M+H)$^+$, RT 2.62 minutes (Method 3).

Example 5

2-[(3S)-3-{[5-(Azetidin-1-ylcarbonyl)-1-methyl-1H-indol-3-yl]methyl}morpholin-4-yl]-6,6-dimethyl-6,7-dihydro[1,3]thiazolo[5,4-c]pyridin-4(5H)-one The title compound was prepared from Intermediate 24 and azetidine hydrochloride according to Method O (with the addition of 1.2 equivalents of DIPEA) and was isolated as a white solid (65%) after purification by column chromatography (SiO$_2$, 0-6% MeOH/DCM). $\delta_H$ (CD$_3$OD) 8.19 (1H, d, J 1.0 Hz), 7.50 (1H, dd, J 8.6 and 1.6 Hz), 7.40 (1H, d, J 8.6 Hz), 7.18 (1H, s), 4.53-4.45 (2H, m), 4.36-4.28 (1H, m), 4.29-4.18 (2H, m), 4.11-4.01 (1H, m), 3.87 (1H, d, J 11.8 Hz), 3.79 (3H, s), 3.74-3.55 (4H, m), 3.39 (1H, dd, J 13.9 and 10.2 Hz), 3.10 (1H, dd, J 13.9 and 4.9 Hz), 2.84 (2H, s), 2.44-2.35 (2H, m), 1.38 (3H, s), 1.37 (3H, s). Exchangeable proton was not observed. LCMS (ES+) 494.3 (M+H)$^+$, RT 2.59 minutes (Method 3).

Example 6

3-{[(3S)-4-(6,6-Dimethyl-4-oxo-4,5,6,7-tetrahydro[1,3]thiazolo[5,4-c]pyridin-2-yl)morpholin-3-yl]methyl}-N,N,1-trimethyl-1H-indole-5-carboxamide The title compound was prepared from Intermediate 24 and dimethylamine (40% v/v in water) according to Method O (in MeCN) and was isolated as a white solid (92%) after purification by column chromatography (SiO$_2$, 0-6% MeOH/DCM). $\delta_H$ (CD$_3$OD) 8.07 (1H, d, J 1.0 Hz), 7.41 (1H, d, J 8.5 Hz), 7.27 (1H, dd, J 8.5 and 1.6 Hz), 7.18 (1H, s), 4.39-4.29 (1H, m), 4.13-4.01 (1H, m), 3.88 (1H, d, J 11.7 Hz), 3.79 (3H, s), 3.75-3.55 (4H, m), 3.39 (1H, dd, J 13.9 and 10.1 Hz), 3.14 (6H, br. s), 3.12-3.02 (1H, m), 2.80 (2H, s), 1.37 (6H, s). Exchangeable proton was not observed. LCMS (ES+) 482.3 (M+H)$^+$, RT 2.57 minutes (Method 3).

Example 7

Methyl 3-{[(3S)-4-(6,6-dimethyl-4-oxo-4,5,6,7-tetrahydro[1,3]thiazolo[5,4-c]pyridin-2-yl)morpholin-3-yl]methyl}-1-benzofuran-5-carboxylate The title compound was prepared from Intermediate 28 (dissolved in MeOH) according to Method J and was isolated as a white solid (44%) after purification by column chromatography (SiO$_2$, 60-100% EtOAc/hexanes). $\delta_H$ (CD$_3$OD) 8.59 (1H, d, J 1.4 Hz), 7.93 (1H, dd, J 8.7 and 1.7 Hz), 7.69 (1H, s), 7.44 (1H, dd, J 8.7 and 0.4 Hz), 4.55-4.39 (1H, m), 4.05-3.94 (1H, m), 3.89 (3H, s), 3.82 (1H, d, J 11.9 Hz), 3.70-3.40 (4H, m), 3.35-3.24 (1H, m), 3.08 (1H, dd, J 14.1 and 5.8 Hz), 2.77 (1H, d, J 17.0 Hz), 2.70 (1H, d, J 17.0 Hz), 1.28 (3H, s), 1.25 (3H, s). Exchangeable proton was not observed. LCMS (ES+) 456.1 (M+H)$^+$, RT 2.68 minutes (Method 9).

Example 8

3-{[(3S)-4-(6,6-Dimethyl-4-oxo-4,5,6,7-tetrahydro[1,3]thiazolo[5,4-c]pyridin-2-yl)morpholin-3-yl]methyl}-N,N-dimethyl-1-benzofuran-5-carboxamide The title compound was prepared from Intermediate 30 and dimethylamine (40% v/v in water, 3 mL) according to Method O and was isolated as a white solid (33% from Intermediate 29) after purification by column chromatography (SiO$_2$, 0-4% MeOH/DCM). $\delta_H$ (CD$_3$OD) 8.16 (1H, d, J 1.3 Hz), 7.76 (1H, s), 7.54 (1H, dd, J 8.5 and 0.4 Hz), 7.39 (1H, dd, J 8.5 and 1.7 Hz), 4.55-4.45 (1H, m), 4.14-4.01 (1H, m), 3.90 (1H, d, J 11.9 Hz), 3.79-3.59 (3H, m), 3.59-3.49 (1H, m), 3.45-3.34 (1H, m), 3.24-3.00 (7H, m), 2.81 (1H, d, J 16.9 Hz), 2.75 (1H, d, J 16.9 Hz), 1.37 (3H, s), 1.35 (3H, s). Exchangeable proton was not observed. LCMS (ES+) 469.1 (M+H)$^+$, RT 1.95 minutes (Method 9), RT 1.50 minutes (Method 10).

Example 9

2-[(3S)-3-{[5-(Azetidin-1-ylcarbonyl)-1-benzofuran-3-yl]methyl}morpholin-4-yl]-6,6-dimethyl-6,7-dihydro[1,3]thiazolo[5,4-c]pyridin-4(5H)-one The title compound was prepared from Intermediate 30 and azetidine hydrochloride (40% v/v in water, 3 mL) according to Method O (with the addition of 1.2 equivalents of DIPEA) and was isolated as a white solid (28% from Intermediate 29) after purification by column chromatography (SiO$_2$, 0-4% MeOH/DCM, followed by SiO$_2$, 0-5% MeOH/EtOAc). $\delta_H$(CD$_3$OD) 8.27 (1H, d, J 1.3 Hz), 7.77 (1H, s), 7.61 (1H, dd, J 8.6 and 1.7 Hz), 7.53 (1H, d, J 8.6 Hz), 4.53-4.45 (3H, m), 4.36-4.28 (2H, m), 4.15-4.02 (1H, m), 3.89 (1H, d, J 11.9 Hz), 3.77-3.54 (4H, m), 3.37 (1H, m), 3.12 (1H, dd, J 14.0 and 5.4 Hz), 2.85 (1H, d, J 16.8 Hz), 2.79 (1H, d, J 16.8 Hz), 2.44-2.35 (2H, m) 1.37 (3H, s), 1.35 (3H, s). Exchangeable proton was not observed. LCMS (ES+) 481.1 (M+H)$^+$, RT 1.89 minutes (Method 9).

Example 10

3-{[(3S)-4-(6,6-Dimethyl-4-oxo-4,5,6,7-tetrahydro[1,3]thiazolo[5,4-c]pyridin-2-yl)morpholin-3-yl]methyl}-1-methyl-1H-indole-5-carbonitrile The title compound was prepared from Intermediate 15 and Intermediate 33 according to Method N and was isolated as a white solid (38%) after purification by column chromatography (SiO$_2$, 0-10% MeOH/EtOAc), followed by preparative HPLC (Method 13). $\delta_H$ (DMSO-d$_6$) 8.45 (1H s), 7.64-7.56 (1H, m), 7.50 (1H, dd, J 8.6 and 1.3 Hz), 7.43 (1H, s), 7.35-7.32 (1H, m), 4.29-4.21 (1H, m), 4.02-3.97 (1H, m), 3.78 (3H, s), 3.74 (1H, d, J 11.9 Hz), 3.60-3.45 (4H, m), 3.32-3.24 (1H, m), 2.93 (1H, dd, J 14.1 and 11.8 Hz), 2.77 (2H, s), 1.26 (6H, s). LCMS (ES+) 436.2 (M+H)$^+$, RT 2.37 minutes (Method 12).

Example 11

3-{[(3S)-4-(6,6-Dimethyl-4-oxo-4,5,6,7-tetrahydro[1,3]thiazolo[5,4-c]pyridin-2-yl)morpholin-3-yl]methyl}-1-methyl-1H-indole The title compound was prepared from Intermediate 15 and Intermediate 37 according to Method N and was isolated as a white solid (39%) after purification by preparative HPLC (Method 13). $\delta_H$(DMSO-d$_6$) 7.77 (1H, d, J 8.8 Hz), 7.39 (1H, d, J 8.1 Hz), 7.32 (1H, s), 7.20 (1H, s), 7.23-7.10 (1H, m), 7.06 (1H, s), 4.06-3.99 (1H, m), 4.10-3.85 (1H, m), 3.72 (3H, s), 3.70-3.60 (1H, m), 3.56-3.54 (2H, m), 3.49-3.47 (1H, m), 3.33-3.31 (2H, m), 2.85 (1H, dd, J 13.8 and 4.0 Hz), 2.73 (2H, d, J 3.2 Hz), 1.26 (6H, s). LCMS (ES+) 411.2 (M+H)$^+$, RT 2.49 minutes (Method 12).

Example 12

Method AI

2-[(3S)-3-(1-Benzofuran-3-ylmethyl)morpholin-4-yl]-6,6-dimethyl-6,7-dihydro[1,3]thiazolo[5,4-c]pyridin-4(5H)-one To a stirred solution of Intermediate 38 (0.25 g, 0.53 mmol) in 1,4-dioxane (4 mL) was added a solution of lithium hydroxide monohydrate (0.047 g, 1.11 mmol) in water (2 mL). The reaction mixture was stirred at 60° C. for 2 h. EtOAc (20 mL) was added. The organic fraction was separated, washed with water (3×5 mL), dried (MgSO$_4$), filtered and concentrated in vacuo. Purification by column chromatography (SiO$_2$, EtOAc), followed by preparative HPLC (Method 13), gave the title compound (0.050 g, 24%) as a white solid. $\delta_H$ (CDCl$_3$) 7.92-7.90 (1H, m), 7.56 (1H, s), 7.51-7.50 (1H, m), 7.36-7.30 (2H, m), 5.17 (1H, s), 4.30-4.28 (1H, m), 4.09-4.07 (1H, m), 3.90-3.87 (1H, m), 3.74-3.57 (4H, m), 3.42-3.36 (1H, m), 3.03-2.98 (1H, m), 2.87-2.86 (2H, m), 1.41 (6H, m). LCMS (ES+) 398.2 (M+H)$^+$, RT 2.50 minutes (Method 12).

Example 13

3-{[(3S)-4-(6,6-Dimethyl-4-oxo-4,5,6,7-tetrahydro[1,3]thiazolo[5,4-c]pyridin-2-yl)morpholin-3-yl]methyl}-1-benzofuran-5-carbonitrile The title compound was prepared from Intermediate 15 and Intermediate 42 according to Method N and was isolated as a white solid (15%) after purification by preparative HPLC (Method 13). $\delta_H$ (CDCl$_3$) 8.65 (1H, s), 7.66-7.55 (3H, m), 5.27 (1H, s), 4.52-4.40 (1H, d, J 10.6 Hz), 4.11-4.08 (1H, d, J 11.3 Hz), 3.90-3.50 (4H, m), 3.43-3.30 (2H, m), 3.02 (2H, s), 3.00-2.90 (1H, d, J 13.7 Hz), 1.44 (6H, s). LCMS (ES+) 423.3 (M+H)$^+$, RT 2.32 minutes (Method 12).

The invention claimed is:
1. A pharmaceutical composition comprising 3-{[(3S)-4-(6,6-dimethyl-4-oxo-4,5,6,7-tetrahydro[1,3]thiazolo[5,4-c]pyridin-2-yl)morpholin-3-yl]methyl}-N,N,1-trimethyl-1H-indole-5-carboxamide or a pharmaceutically acceptable salt thereof, in association with a pharmaceutically acceptable carrier.
2. A compound which is 3-{[(3S)-4-(6,6-dimethyl-4-oxo-4,5,6,7-tetrahydro[1,3]thiazolo[5,4-c]pyridin-2-yl)morpholin-3-yl]methyl}-N,N,1-trimethyl-1H-indole-5-carboxamide or a pharmaceutically acceptable salt thereof.

* * * * *